(12) United States Patent
Galvan et al.

(10) Patent No.: US 6,492,120 B1
(45) Date of Patent: Dec. 10, 2002

(54) NUCLEIC ACID HYBRIDIZATION ASSAY UTILIZING TRICYCLIC TARGET AND SIGNAL AMPLIFICATION

(75) Inventors: Barbara Galvan, Ventura, CA (US); Jozsef Hepp, Camarillo, CA (US); Ih Chang Hsu, Baltimore, MD (US); Zsolt Lengyel, Camarillo, CA (US); Rajiv Pande, Acton, MA (US); James W. Shih, Bethesda, MD (US)

(73) Assignees: University of Maryland, Baltimore, MD (US); Medical Analysis Systems, Inc., Camarillo, CA (US)

( * ) Notice: Subject to any disclaimer, the term of this patent is extended or adjusted under 35 U.S.C. 154(b) by 0 days.

(21) Appl. No.: 09/705,417

(22) Filed: Nov. 2, 2000

(51) Int. Cl.$^7$ ............... C12Q 1/68; C07H 21/02; C07H 21/04
(52) U.S. Cl. ............... 435/6; 536/23.1; 536/24.3
(58) Field of Search ............... 435/6; 536/23.1, 536/24.3; 935/76, 77, 78

(56) References Cited

U.S. PATENT DOCUMENTS

| | | | |
|---|---|---|---|
| 4,699,876 A | 10/1987 | Libeskind | 435/5 |
| 5,352,775 A | 10/1994 | Albertsen et al. | 536/23.1 |
| 5,462,871 A | 10/1995 | Boon-Falleur et al. | 435/240.2 |
| 5,470,723 A | 11/1995 | Walker et al. | 435/91.2 |
| 5,494,796 A | 2/1996 | Spears et al. | 435/6 |
| 5,500,341 A | 3/1996 | Spears | 435/6 |
| 5,508,168 A | 4/1996 | Orle et al. | 435/6 |
| 5,512,444 A | 4/1996 | Patard et al. | 435/6 |
| 5,518,884 A | 5/1996 | Spears et al. | 435/6 |
| 5,527,676 A | 6/1996 | Vogelstein et al. | 435/6 |
| 5,529,780 A | 6/1996 | Paoletti et al. | 424/199.1 |
| 5,532,108 A | 7/1996 | Vogelstein | 435/240.2 |
| 5,534,438 A | 7/1996 | Hayden et al. | 435/320.1 |
| 5,536,636 A | 7/1996 | Freeman, Jr. et al. | 435/6 |
| 5,536,638 A | 7/1996 | Rossau et al. | 435/6 |
| 5,858,665 A | * 1/1999 | Hepp et al. | |
| 6,114,117 A | * 9/2000 | Hepp et al. | |

OTHER PUBLICATIONS

Bekkaoui, F. et al. (1996). *Bio Techniques*, 20: 240–248.
Gingeras, T.R. et al (1987). *Nucleic Acids Res.* 15: 5373–5390.
Hermanson, Greg T. et al. (1990). *Bioconjugate Techniques*. Academic Press, New York, New York, pp. 55.
Hsu, Ih–Chang et al.(1998). *Anal. Biochem.* 261:219–222.
Hsu, Ih–Chang et al. (1994). *Carcinogenesis* 15:1657–1662.
Lu, A–Lien and Chang, Dau–Yin. (1988). *Cell* 54:805–812.
Lund, V. et al (1988). *Nucl. Acids Res.* 16: 10861–10880.
Wilchek, M. and Bayer, E.A. (1988). *Anaytical. Biochemistry* 171(1):1–32.
Nelson, et al. (1992). *Nonisotopic DNA Probe Techniques*. Academic Press, New York, New York, pp. 274–310.
Saiki et al. (1988). *Science* 239: 487–491.
Southern, E.M. (1975). *J Mol. Biol.* 998:503–517.
Urdea, M.S. et al. (1993). *Clin. Chem.* 39: 725–726.
Wojeiech, J. S. et al *J. Am. Chem. Soc.* (1984). 106:6077–6079
Wu, D. Y. et al. (1990). *Genomics* 4: 560–569.

* cited by examiner

Primary Examiner—Ethan C. Whisenant
(74) Attorney, Agent, or Firm—Morrison & Foerster LLP (57) ABSTRACT

This invention relates generally to nucleic acid-based diagnostic assays for detecting, identifying and/or quantitating target sequences in a sample. More specifically, the invention utilizes sequential cleavage of nucleic acids to achieve target and signal amplification through cycling reactions.

15 Claims, 6 Drawing Sheets

Probe STEM-LOOP STRUCTURE:

```
                15        10
         gtggtagttaAtQccttcgaca 5'
         |||||
      t< tatagccaatt-F 3'
                34        29
```

G = -2.0 kcal/mol
loop Tm = 50°C

FIG. 6

NUCLEIC ACID HYBRIDIZATION ASSAY UTILIZING TRICYCLIC TARGET AND SIGNAL AMPLIFICATION

STATEMENT OF RIGHTS TO INVENTIONS MADE UNDER FEDERALLY SPONSORED RESEARCH

This invention was supported in part by a Cooperative Research and Development Agreement TDCB 648, between the NIHCC, the University of Maryland and Medical Analysis Systems Inc. The government may have certain rights to this invention.

FIELD OF THE INVENTION

This invention relates generally to nucleic acid-based diagnostic assays for detecting, identifying and/or quantitating target sequences in a sample. More specifically, the invention utilizes sequential cleavage of nucleic acids to achieve target and signal amplification through cycling reactions.

BACKGROUND OF THE INVENTION

Nucleic acid hybridization assays are useful in the detection of particular nucleic acid sequences of interest, also referred to as "target sequences". These target sequences may be characteristic of a particular disease-associated gene, or they may be specific for various organisms or cell types. Accordingly, detection and identification of a particular target sequence can provide diagnostically significant information.

The ability to detect target nucleic acid sequences in a sample by hybridization between a target nucleic acid and a complementary "probe" nucleic acid is the cornerstone of nucleic acid-based diagnostic technologies. These assays can generally be characterized as either "heterogeneous" or "homogeneous." Heterogeneous assays depend on the ability to separate hybridized from non-hybridized nucleic acids. One such assay involves immobilization of either the target or probe nucleic acid on a solid support so that non-hybridized nucleic acids which remain in the liquid phase can be easily separated after completion of the hybridization reaction (Southern, *J. Mol. Biol.*, 98: 503–517 (1975)).

In comparison, homogeneous assays depend on means other than physical separation for distinguishing between hybridized and non-hybridized nucleic acids. The avoidance of a separation step renders homogeneous assays easier to use and, therefore, more desirable. One such homogeneous assay relies on the use of a label attached to a probe nucleic acid that is only capable of generating signal when the target is hybridized to the probe (Nelson, et al., *Nonisotopic DNA Probe Techniques*, Academic Press, New York, N.Y., pages 274–310 (1992)).

One of the most significant obstacles to the development of nucleic acid-based diagnostic assays has historically been a lack of sensitivity. In particular, when the number of copies of the target nucleic acid in a sample are limited, sensitivity becomes very important. Many strategies have been designed to overcome this obstacle, with variable success. Among the most successful strategies are those that involve either target amplification or signal amplification. Target amplification involves increasing sensitivity by exponentially multiplying the number of copies of target sequences in a sample. Examples of target amplification techniques include the polymerase chain reaction, or "PCR" (Saiki, et al., *Science* 239: 487–491 (1988), and ligase chain reaction, or "LCR" (Wu, et al., *Genomics* 4: 560–569 (1990)).

Another method for increasing sensitivity is to amplify the signal generated by a single target/probe hybridization event. This can be accomplished by using branched probes, each capable of generating multiple detectable signals (Urdea, et al., *Clin. Chem.* 39: 725–726 (1993)), or by utilizing cycling probe technology or "CPT," which relies on the ability to generate multiple detectable probes from a single target sequence (Bekkaoui, et al., *BioTechniques*, 20: 240–248 (1996)).

Still another method for increasing the sensitivity of nucleic acid-based diagnostics employs a cascade reaction to amplify signal. U.S. Pat. No. 4,699,876 discloses a heterogeneous assay utilizing a probe with an enzyme activator attached thereto. Once the probe binds to the target and unhybridized probe is removed, the enzyme activator initiates a signal generation cascade that produces amplified signal levels.

Although a variety of assays exist for detecting nucleic acid, the expanding applications of such assays provides a continuous need for further assay innovation to achieve improved sensitivity and ease of use.

SUMMARY OF THE INVENTION

Accordingly, the present invention provides a highly sensitive tricyclic assay system for measuring a target nucleic acid from a sample added to an assay medium, comprising:

a) a non-diffusible first probe-reporter complex, wherein the first probe comprises a nucleotide sequence that is complementary to the target nucleic acid, and wherein the fist probe and the target nucleic acid have sufficient complementarity to hybridize to form a first cleavage site;

b) a first cleavage reagent that recognizes and cleaves the first cleavage site thus forming a diffusable probe fragment-reporter complex and releasing the target nucleic acid into the assay medium;

c) a non-diffusible first target mimic that is functionally separated from the probe reporter complex, wherein the first target mimic comprises a nucleotide sequence that is complementary to the probe, and wherein the first target mimic and probe fragment have sufficient complementarity to hybridize to form a second cleavage site; and d) a second cleavage reagent, which may be the same or different from the first cleavage reagent, that recognizes and cleaves the second cleavage site thus forming a diffusible target mimic fragment and releasing the probe fragment reporter complex into the assay medium;

wherein the target mimic fragment has sufficient complementarity to hybridize to a second probe;

wherein the target nucleic acid after release into the assay medium following cleavage of the first probe remains capable of binding to a second probe; and wherein the probe fragment has sufficient complementarity to hybridize to a second target mimic.

As used herein, the term "complementary" is not intended to be limited to cases in which two nucleic acids that are hybridized are perfectly complementary. Accordingly, when one nucleic acid is referred to as being "complementary" to the other nucleic acid, this term is inclusive of pairs of nucleic acids that, when hybridized together, have one (or more) mismatch(es), so long as they have sufficient complementarity to form stable duplexes.

Other aspects of the invention are described throughout the specification and claims.

DETAILED DESCRIPTION OF THE INVENTION

Assay Overview

Figure 1:
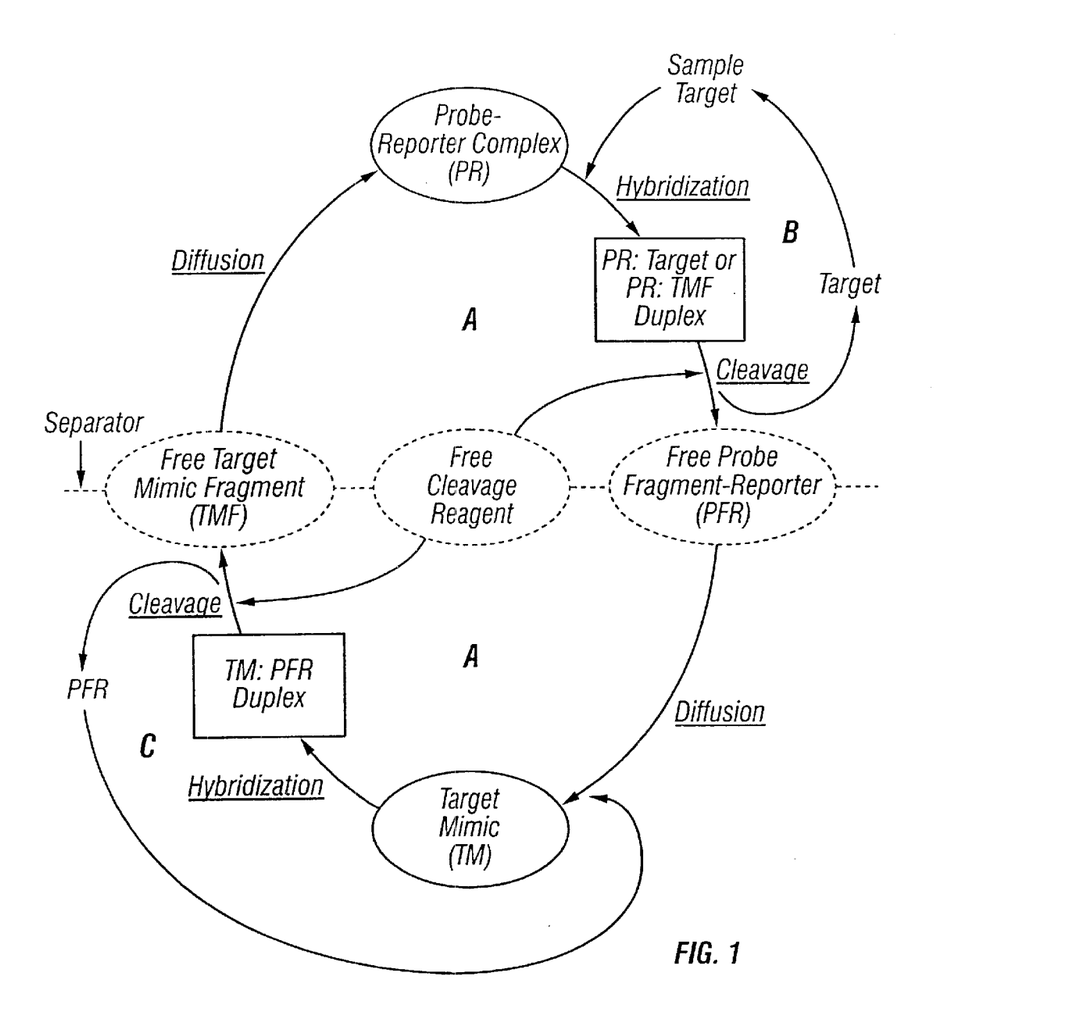
FIG. 1 is a schematic illustration showing the different cycling reactions of the assay method. PR=Probe-Reporter complex; PFR=Probe Fragment-Reporter complex; TM=Target Mimic; and TMF=Target Mimic Fragment.

The present invention relates to a tricyclic assay system for the detection of target nucleic acids. The assay system is depicted in FIG. 1. As shown, this assay consists of three separate cycling reactions. The assay components surrounded by a broken line represent diffusible (free) assay components, whereas the assay components surrounded by solid lines represent non-diffusible (bound or separated) assay components. Also depicted in FIG. 1 is a "separator", which, in one embodiment of the present invention, may be a membrane through which the diffusible but not the non-diffusible assay components may pass.

Accordingly, the three separate cycling reactions may be further described as follows:

A) This is the main cycling reaction and involves the sequential repetition of the following steps:
  i) hybridization of the target (or target mimic fragment, "TMF") to the probe reporter complex ("PR") which results in formation of a cleavage site;
  ii) recognition of the cleavage site and cleavage of the PR complex by the cleavage reagent (such as mutY);
  iii) release of the probe fragment-reporter complex ("PFR") (which, in the case of mutY cleavage is facilitated by using an "amine amplifier");
  iv) hybridization of the released PFR to the target mimic ("TM") which results in formation of a cleavage site;
  v) recognition of the cleavage site and cleavage of the TM by the cleavage reagent (which may be the same or different from the cleavage reagent in step ii);
  vi) release of the target mimic fragment ("TMF") (which, in the case of mutY cleavage is facilitated by using an "amine amplifier");
  Then, the TMF hybridizes to another PR complex to begin the cycle again with step i).

B) Cycling reaction B is perpetuated by the sequential release of target after cleavage of the PR:Target duplex, which is then free to hybridize with another PR complex.

C) Cycling reaction C is perpetuated by the sequential release of PFR after cleavage of the TM:PFR duplex, which is then free to hybridize with another TM.

The combination of these cycling reactions thus amplifies the amount of signal generated by a single target nucleic acid molecule and can eliminate the necessity for a separate amplification step such as PCR which is subject to the influences of contaminating non-target nucleic acids. In addition to being suitable for use to detect a single nucleotide sequence in a sample, it would be readily apparent that the assay could easily be adapted for use to simultaneously detect more than one target nucleic acid by combining more than one signal generating system into the assay system. In addition, it is possible to incorporate an internal control mechanism or detect a second target by having a heterogeneous assay system (i.e. more than on combination of probe/target mimic and reporter) in a single assay vessel, such that one assay system can detect the target nucleic acid while the other assay system in the same vessel can detect a second target or a control nucleic acid using a separate signal generation system.

The tricyclic reaction is carried out in an assay system in which the non-diffusible assay components are physically separated, such as by immobilizing them to separate solid supports, or to separate locations on the same solid support. In the assay system, both solid supports or locations make contact with the assay medium such that cleavage of the duplexed assay components results in release of cleaved fragments from the solid support thereby allowing the cleaved fragments to diffuse through the medium for interaction with the other non-diffusible assay components.

Alternatively, instead of immobilizing to solid supports, the non-diffusible assay components can be added to the assay medium on separate sides of a membrane which is permeable to diffusible assay components, such as the cleaved fragments, but not the uncleaved components. In another embodiment, the assay components can be temporally separated by adding them to the assay medium sequentially. In yet another embodiment, the assay components can be electrochemically separated by using electric forces to control the location and movement of charged assay components. These and other assay formats are more fully described below.

Cleavage Reagents

The present invention relies on incorporating a cleavage reagent into the assay system that causes the cleavage of duplexed assay components and subsequent release of cleaved fragments as depicted in FIG. 1. In a preferred embodiment, the cleavage reagent is specific for mismatched bases. As used herein "mismatch" is an incorrect pairing between the bases of two nucleotides located on complementary strands of DNA, i.e., base pairs that are not A:T or G:C paired. Mismatch cleavage reagents include mismatch cleavage enzymes (or functionally homologous proteins, such as mutM) and other reagents such as proteins, organic or inorganic reagents that can specifically recognize and cleave a base pair mismatch. In addition, certain base modifications can be incorporated into the cleavage site, and such modified bases will be recognized and cleaved in the same way that a mismatched base is removed, even though they are not, per se, mismatched.

Unlike restriction enzymes, which are specific to recognition sites of approximately 4–6 bp, the use of mismatch cleavage reagents does not restrict detection to limited sequences along the target nucleic acids. A mismatch site between the probe and target nucleic acid, for example, is simple to create for almost any base along the target nucleic acid sequence. Furthermore, in contrast to restriction enzymes which normally cleave double-stranded DNA, mismatch cleavage reagents, such as mutY, are specific to only one strand of a mismatched hybrid. For example, mutY will only cleave at the "A" of an "A/G" mismatch. This allows for the uncleaved, hybridized strand to be released, in the presence of an amine amplifier, and recycled.

The utilization of mismatch cleavage reagents is also advantageous over the use of RNaseH because it allows for direct detection of RNA targets while employing DNA probes. This eliminates the need to reverse transcribe the RNA targets to cDNA prior to target amplification and detection. Subsequently, the assay is simpler and less time-consuming to perform. In addition, the use of DNA-based probes rather than RNA-based probes decreases the risks of degradation due to endogenous and exogenous RNases that are difficult to inactivate.

Accordingly, in a preferred embodiment, the instant invention uses mutY, an A/G specific endonuclease that cleaves the phosphodiester bond at 3' and/ or 5' end of the mismatch A. This enzyme does not cleave single stranded nucleic acid (Lu and Chang, Cell, 54:805–812 (1988)). This A/G specific enzyme is identified as the gene product of the mutY (or micA) locus of E. coli. There are now over 10 enzymes in this group identified in bacteria and animal cells. This group of enzymes has three common functions, i.e 1) the glycosylase activity to remove the mismatched A; 2) the lyase activity to cleave the resulting apurinic/apyramidinic (AP) site; and 3) binding to the mismatch to form a complex that inhibits the spontaneous dissociation of the target from the mismatch-cleaved probe. Upon target hybridization, the mechanism for mismatch cleavage first involves the glycosylase activity which removes the mismatched A to open up the deoxyribose ring and create the AP site. One of the amino groups of the enzyme then attacks the $-C=O$ group to form Schiff's base resulting in the binding and B-elimination for nicking the phosphodiester bond. Therefore, mutY has the functions of an adenine glycosylase and also an A/G mismatch specific endonuclease. Amine amplifiers, including primary and secondary amines, compete with the amines of the mutY protein, block the binding of mutY protein and the nucleic acid substrate, and thus free the target (or TMF) and the PFR for recycling. Suitable amine amplifiers include, for example, ammonium acetate or amine derivatives such as piperidine, diethylamine and ammonium carbonate.

When a DNA probe hybridizes to a nucleic acid target and generates a G/A mismatch in the probe-target DNA duplex, the mismatch repair enzyme, for example mutY, will specifically cleave the "A" strand (probe) by breaking the phosphodiester bonds on both sides (i.e. the 3' and 5' side) of the mismatch "A". This specific cleavage only at the mismatched "A" of the probe by mutY only when hybridized to the complementary target allows for specific identification of the target. Thus the detection of the mismatch base and the complementary nucleic acid target is the fundamental enzyme function of mismatch repair enzymes such as mutY, (a mismatch specific adenine N-glycosylase), or a mismatch specific thymine N-glycosylase, etc. The target can be DNA or RNA.

Another enzyme contemplated to be useful in the practice of the instance invention is a T/G mismatch specific endonuclease. This enzyme was identified as T/G mismatch specific thymine N-glycosylase and has been proven to cleave reliably the phosphodiester bond of T at the T/G mismatch in identification of gene mutations (Hsu et al., Carcinogenesis, 15:1657–1662 (1994)).

Target Nucleic Acid

The target nucleic acid sequence, which may be DNA or RNA, will generally be chosen such that it is characteristic of, or associated with, a particular organism, cell type or gene. Accordingly, detection of the target nucleic acid in the sample would implicate a particular organism, cell type or gene as the source of the target nucleic acid. Selection of the appropriate target nucleic acid sequence would necessarily depend on the goal to be achieved by performing the assay. For example, if the sample was a biological fluid suspected of containing a particular group of organism (kingdom, phylum, family, genus or species), a target nucleic acid sequence would be chosen which was specific for this group of organism.

Many target nucleic acid sequences are known and would be suitable for detection using the method of the present invention. They include sequences that are characteristic of pathogenic bacteria and viruses, as well as sequences associated with tumor-specific antigens and mutant alleles. For example, sequences have been described that serve as targets for the detection of *Mycobacterium kansasii*. (U.S. Pat. Nos. 5,500,341; and 5,518,884). Other target sequences that are characteristic of different mycobacterial species have also been described. (U.S. Pat. Nos. 5,494,796; 5,500,341; and 5,470,723). The spacer region between the 16S and 23S rRNA genes of *Neisseria gonorrhoeae* has served as a target sequence for specific detection this pathogen. (U.S. Pat. No. 5,536,638). Among the viral nucleic acids that serve as target sequences and are thus useful in the detection of these organisms are canine herpesviruses GB and GC, and herpes simplex virus. (U.S. Pat. Nos. 5,529,780; and 5,508,168). Tumors and tumor metastases can be monitored by detecting genes encoding tumor-associated antigens. A nucleic acid sequence that was associated with neoplastic disease and thus was targeted in a probe-based assay was a gene encoding an abnormal tyrosine phosphatase. (U.S. Pat. No. 5,536, 636). Genes encoding bladder tumors associated antigens have also been targeted. (U.S. Pat. Nos. 5,512,444; and 5,462,871). Detection of mutant alleles can allow predictions of a disease course or of propensity toward a given disease. A mutant allele associated with Huntington's disease has been targeted in probe-based assays, as has the APC gene associated with certain colorectal cancers. (U.S. Pat. No. 5,534,438; and U.S. Pat. No. 5,352,775). In other cases, nucleic acid sequences in genes that have undergone deletions have served as the targets for probe-based assays. (U.S. Pat. Nos. 5,532,108; and 5,527,676).

Using the diagnostic method of the present invention, it is possible to detect the presence of a particular target nucleic acid sequence in a sample. Conversely, it is also possible to determine that a particular target sequence is absent. If a target sequence is detected, it is also possible to identify the target sequence based on its ability to hybridize with the particular probe nucleic acid being used. In turn, this enables the identification of a particular cell type, organism, or gene sequence with which the target sequence is specifically associated. It is also possible to quantify the amount of target sequence present based on the amount of signal generated during the assay. Additionally, if the amount of target sequence per cell or organism is known, it is possible to quantify the number of cells or organisms present in the sample.

Sample

The sample may take a variety of forms, including liquid such as water, whole blood, serum, plasma or urine; or solid such as dust, soil, food, or tissue samples. The nucleic acid in the sample must be made available to contact the probe nucleic acid before any hybridization can occur. This generally necessitates at least partial purification of nucleic acid from other biomolecules, such as proteins, lipids, and other cellular components which may be present in the sample, before carrying out the assay. Methods of purifying nucleic acids from biological and non-biological samples are described in the scientific literature and can easily be selected for use depending on the source of the sample and the desired degree of purity. Many of these methods are commercially available in the form of kits.

Hybridization conditions will also influence the necessity for sample purification. When less stringent hybridization conditions are utilized, a more purified sample preparation is generally needed. When more stringent hybridization conditions are utilized, a less purified sample preparation is needed. The effects of various hybridization conditions have been described in the literature. See, for example, Sambrook, et al., *Molecular Cloning: A Laboratory Manual*, Cold Spring Harbor Laboratory Press, Chapter 11 (2d ed. 1989).

Target nucleic acids can be single- or double-stranded. If the target nucleic acid is initially double-stranded, it can be made single-stranded by known methods such as heating, low ionic strength, high pH (for DNA), etc. The target nucleic acid can also be DNA, RNA or a chimera of DNA and RNA.

When the target nucleic acid is RNA, a cDNA copy of the RNA can be generated using reverse transcriptase and an appropriate primer prior to initiation of the assay. In this embodiment, the probe is designed to be complementary to the cDNA generated with reverse transcriptase. However, one of the features of the present invention is that it can be used to detect the original RNA target nucleic acid in a sample, thus eliminating the need for transcription of the RNA into cDNA.

Probe and Target Mimic Preoaration

The probe and target mimic nucleic acids can be either DNA or RNA. They can be prepared chemically or enzymatically by any known method. Enzymatic synthesis can be achieved in vivo using cloning techniques, or in vitro using appropriate polymerase enzymes and substrates. Chemical synthesis is preferred, and can be performed using any known method, such as the method described by Stec, et al. (*J. Am. Chem. Soc.* 106: 6077–6079 (1984)) using the phosphoramidite method and an automated synthesizer, such as Model 380-B from Applied Biosystems, Inc. (Foster City, Calif.).

The assay of the present invention depends on the ability of target and target mimic to hybridize with probe. Once a target nucleic and sequence has been selected, either from the literature or from isolating and sequencing the target from a source of nucleic acid, the probe and target mimics are designed to have the appropriate nucleic acid sequence. In other words, the nucleic acid sequence of the probe will necessarily be complementary to the nucleic acid sequence of the target, and the nucleic acid sequence of the target mimic will necessarily be complementary to the nucleic acid sequence of the probe.

The length of the probe and target mimic nucleic acids will be any length which is sufficient to form specific and stable hybrids with their complementary nucleic acids. For example, the target mimic must be sufficiently long and have a sequence which will allow it to form a stable hybrid with the probe, but it is not necessary that it have the same length or sequence as the target nucleic acid. It is also possible that the target mimic can have the same sequence and length as the target nucleic acid. The probe nucleic acid must also be of sufficient length and have a sequence which will allow it to form a specific and stable hybrid with both the target and the target mimic nucleic acid.

The nucleic acids are also preferably designed such that the assay temperature is set between the melting point (Tm) of the nucleic acid hybrids prior to cleavage by the mismatch cleavage reagents, and the Tm of the hybrids following cleavage. When the cleavage reagent is mutY, in the presence of amine amplifiers, this design allows for the release and cycling of the cleaved nucleic acids (Hsu et al., Anal. Biochem., 261:219–222).

Signal Generation

The way in which signal is generated in the assay system depends on the choice of reporter. As used herein, a "reporter" is a molecule or moiety that either indirectly or directly generates a detectable signal. For example, the reporter may be an enzyme that catalyzes a calorimetric reaction. Many different known methods for generating signal from the hydrolysis of biomolecules are well known in the art and can easily be adapted for use in the assay systems of the present invention.

Examples of enzyme-substrate pairs include amyloglycosidase-amylose dyes, proteases and macromolecular substrates, galactosidase and macromolecular substrates, trypsinogen and its substrate, trypsin and its substrate, etc. For example, if the reporter is trypsin, the substrate Z-Gly-Pro-Arg-pNA (Sigma Chemical Co., Milwaukee, Wis.) can be used. It is also possible to amplify the reaction even further by attaching a second (same or different) reporter to the target mimic, such that the reporter remains attached to the target mimic fragment after cleavage by the cleavage reaction. Using trypsinogen as one of the reporters and enterokinase as the other reporter, release of the enterokinase can effectuate cleavage of the trypsinogen to form active trypsin which then generates a calorimetric signal from its substrate that is spectrophotometrically detectable at 405 nm.

Separation of Non-Diffusible Assay Components

The method of the present invention is performed in an "assay system", i.e. an assay compartment or vessel which contains physical or other means for separating the non-diffusible assay components from one another.

It is important that the assay system provides for separation of the probe and the uncleaved target mimic, so that the target mimic does not initiate the main cycling reaction in the absence of sample target. See FIG. 1. Otherwise, signal generation would occur in the absence of sample target and result in a false positive result.

This separation can be achieved in a solid-support system by attaching the probe-reporter complex to one surface, and the target mimic to another surface. Alternatively, these assay components can be separated by a membrane which is specially designed to separate the uncleaved assay components from their corresponding free forms, as depicted in FIG. 1. When such a membrane is utilized, it may be desirable to couple both the probe-reporter complex and the target mimic to a membrane impermeable macromolecule in order to facilitate separation by the membrane.

Examples of solid support materials are, for example, nitrocellulose, polystyrene, nylon, glass, silica or polymethacrylate. Examples of permeable membrane materials are, for example, cellulose, derivatized cellulose (nitrocellulose, cellulose-acetate), and nylon. The choice of separation mechanism can easily be made based on the characteristics (size, molecular weight, etc.) of the non-diffusible assay components to be separated. Many known examples of appropriate solid support systems and membrane systems are known in the relevant art.

Attachment of the probe (either before or after it is complexed with the reporter) and the target mimic can be performed using known techniques. Attachment can be covalent or ionic, or involve affinity/non-covalent interactions, such as binding pairs. For example, avidin-biotin binding systems can be easily adapted for use in the assay system of the present invention. In one embodiment, a biotinylated nucleic acid (probe or target mimic) can be attached to an avidinylated surface as described by M. Wilchek and E. A. Bayer, *Anal. Biochem*, 171(1): 1–32 (1988).

Ionic attachment can be accomplished by binding the negatively charged nucleic acid probe to a positively charged surface, such as nitrocellulose or nylon (Gingeras, et al., *Nucleic Acids Res*. 15: 5373–5390 (1987).) Covalent attachments of nucleic acids to solid supports are described in *Bioconjugate Techniques*, Hermanson, et al., Academic Press, New York N.Y., page 55 (1990).

Covalent attachment of the probe to a solid support generally involves modification of the probe at either the 5' or 3' terminus. Terminal modification is preferred in order to lessen interference with target (and target mimic) hybridization to the probe. For example, the 5' terminus can be modified by introducing reactive amine moieties (using an automated synthesizer) which can then be used in a coupling reaction with activated supports. Examples of other methods of attachment involve carbodiimide based attachment of nucleic acids to cellulose, sephadex or sephacryl; and immobilization of the nucleic acid via the nucleic acid bases which are coupled to the solid support, and vice versa (Lund, et al., *Nucl. Acids Res*. 16: 10861–10880 (1988).)

It is also possible to use a glass or plastic assay compartment as one surface, and a microsphere placed inside the glass assay compartment as the second surface. Both surfaces can then be activated using known methods, and used as a platform for attachment of the target mimic to one surface, and the probe-reporter complex to the other surface.

Yet another form of separation can be achieved by sequential exposure of the assay medium containing the sample target to the probe-reporter complex and the target mimic. In addition, the assay system can be dry until addition of a liquid sample, or a liquid medium can be supplied and added either before, during or after sample addition.

Applications of the Assay Method

As described above, the present tricyclic assay system can be used to improve assay sensitivity over non-cycling assay systems. This added sensitivity can eliminate the need for separate target amplification reactions such as PCR, and makes the assay particularly well-suited for applications where the concentration of target in the sample is minimal, such as would be expected for the amount of pathogen-associated nucleic acids in the early stages of an infectious disease.

The method of the present invention is useful for detecting the presence of a nucleic acid having a particular sequence in a sample (the "target nucleic acid".) The target nucleic acid may be associated with a genetic disease, such as cystic fibrosis or fragile X chromosome, in which case the assay could be used to indicate a predisposition for this disease or to confirm a diagnosis of the disease. Alternatively, the present method may also be used for detecting the presence of organisms associated with pathogenicity, such as mycoplasma, yeast, bacteria and viruses. In addition, it may be used to detect the presence of cancer-associated nucleic acid sequences, such as oncogenes. The present invention may also be used to monitor the sensitivity of different organisms or cell types to treatments, or to detect antibiotic resistance traits in organisms when these traits are associated with particular nucleic acid sequences. In a laboratory setting, the present invention may also be useful to confirm the presence of a particular target nucleic acid sequence, or to test for hybridization of a target nucleic acid sequence prepared in the laboratory with a complementary probe nucleic acid sequence.

EXAMPLES

Example 1

Detection of a Gene Mutation

For clarity purposes this section is divided into 4 subsections. These are, (a) design of the probe reporter complex (PR) and target mimic (TM) entity assemblies, (b) the assay reaction, (c) detection of the target of interest, and (d) conclusion.

(a) Design of the PR complex and TM entity

Sequence Selection

Cultured human hepatoma cell line, HuH7 cells were used as the source of target. The HuH7 cells have an "A" to "G" p53 mutation at codon 220 position 2 (exon 6) and produce mRNA with a "G" at that site. The probe sequence was obtained from the above mentioned target sequence and modified to incorporate a mutY specific mismatch. The modified sequence of PR was thus, 5' biotin-GAC TGG CGG CTC AAA GGG CAC GAC ACT ATG TC-3' (Seq. ID 1). This oligonucleotide was synthesized by the Biopolymer Lab, , Baltimore, Md.). The incorporation of mismatch had some constraints; (a) under appropriate temperature conditions, 37° C., the mismatch is to allow for dissociation of the cleaved fragment (Tm requirements directly related to sequence length), and (b) the mismatch site should not be sterically hindered.

The TM entity design was similar to the PR complex design, especially with regard to the mismatch incorporation. The actual sequence used was 5' biotin -GAC TTT CGA CAT AGT GTA GTG CCC TGT GAG CCG-3' (Seq. ID 2), and the oligonucleotide was synthesized by the Biopolymer Lab, (UMAB, Baltimore, Md.).

The sequence of the target was as follows: 5' -GCC GAG TGT CCC GTG-3' (Seq. ID 3). The target was synthesized by the Biopolymer Lab, (UMAB, Baltimore, Md.).

Radiolabeling the probe

The probe oligonucleotide (PR complex) was labeled with $^{32}P$ at 5' end by T4 kinase reaction using a commercially available kit (Amersham Pharmacia Biotech, Piscataway, N.J.).

Immobilization of the PR complex and TM:

All immobilization, rinses and washes were performed in 0.6-ml microcentrifuge tubes. Immobilization of the PR complex and TM entity was performed on streptavidin coated magnetic microspheres (Dynal Inc. Lake Success, N.Y.). Magnetic particles (1.8 mg) were rinsed in mutY reaction buffer (10 mM Tris, pH 7.6, 50 mM ammonium acetate, 10 ug/ml acetylated BSA, 1 mM EDTA) and re-suspended in the same buffer. Out of this suspension, 0.9 mg of beads were aliquoted and 2.7 pmol $^{32}P$ labeled PR were added. Separately, 0.6-mg beads were aliquoted and 1.8 pmol TM was added. Both sets of beads (PR complex and TM containing) along-with the remaining 0.3 mg (referred to as control beads) were incubated at 37° C. for 30 min. Following incubation, the beads were rinsed with mutY reaction buffer four (4) times.

(b) The assay reaction

In a series of reaction tubes containing varying amounts of target (100 fmol, 10 fmol, 1 fmol, 100 amol, 10 amol, zero) in duplicate, 30 ug of PR complex beads were added. To each set of the tube containing identical target concentration either 30 ug TM beads or 30 ug control beads were added. A 2 ul aliquot of mutY (5 ng/ml) was added and the reaction volume brought up to 27 ul with mutY reaction buffer. The tubes were allowed to incubate for 3.5 hours, at 37° C.

(c) Detection

Following incubation, the supernatant was aliquoted and subjected to 20% polyacrylamide gel electrophoresis, and visualized. Target detection or detection of the cleaved activator-reporter (which is a function of target presence/identification) was performed via autoradiography. This enabled not only the identification of the cleaved product, but also revealed the cleaved fragment size and provided conclusive evidence of specific cleavage at the designed mismatch site. Detection of $^{32}P$ on the gel was accomplished by the direct exposure of the gel on to an X-ray film.

(d) Conclusion

MutY cleavage of the PR complex (hybridized to target) was demonstrated (data not shown). Cleavage occurred specifically at the AIG mismatch (as determined by the PAGE-observed PFR size). The 10-amol target level is detectable when TM beads are included in the assay reaction. This is approximately a 1000-fold improvement in the target detection limit, when compared to the detection limit achieved with no TM beads included in the assay. These results demonstrate that the TM plays a significant role in signal amplification.

Example 2

Detection of HIV-1

This section is also divided into 4 subsections. These are, (a) design of the probe reporter complex (PR complex) and target mimic (TM); (b) the assay reaction; (c) detection of the target of interest; and (d) conclusion. The notable difference between this example and Example 1, aside from the different target sequence, is the utilization of a non-isotopic detection methodology.

(a) Design of the PR complex and TM entity

Sequence Selection

The HIV probe sequence was selected hybridizes to a target sequence located in a highly conserved gag region of the HIV-1 gene. The probe sequence was modified to incorporate a mutY specific mismatch. The sequence of PR was the following: 5' biotin-ACA GCT TCC TAA TTG ATG GTG TTA TAG CC-fluorescein 3' (Seq. ID 4). This oligonucleotide was synthesized by Midland Certified Reagent Company, (Midland, Tex.).

This incorporated mismatch would create a mutY recognition and cleavage event of the probe. The TM design was similar to the PR complex design, especially with regard to the mismatch incorporation. The actual sequence used was 5' biotin-TAA GGC TAT AAA ACC ATC AAT GAG GAA GCT GT-3' (Seq. ID 5), and the oligonucleotide was synthesized by Midland Certified Reagent Company (Midland, Tex.).

The sequence of target was as follows: 5'-TAC CAT CAA TGA GGA AGC TG-3' (Seq. ID 6). The target was purchased from Midland Certified Reagent Company (Midland, Tex.).

Immobilization of PR complex and TM

All immobilization, rinses and washes were performed in 0.6 ml microfuge tubes. PR was immobilized onto streptavidin magnetic beads (Dynal Inc., Lake Success, N.Y.). Prior to being used for immobilization, the beads were rinsed in binding buffer (5 mM Tris-HCl, pH 7.5, 0.5 mM EDTA, 1M NaCl, 0.01% (v/v) Tween 20). Immobilization was performed in the binding buffer (33 pmol DNA/mg beads, for 30 min at 37° C., with gentle agitation, in the dark). Likewise, TM was immobilized on separate streptavidin coated magnetic beads, using identical reaction concentrations and conditions.

Following immobilization, the beads were rinsed with binding buffer and washed three (3) times (30 min each, at 37° C.) with the washing buffer (5 mM Tris-HCl, pH 7.5, 0.5 mM EDTA, 1M NaCl, 0.1% (v/v) Tween-20). Prior to being utilized in the assay reaction the washed beads were equilibrated with mutY reaction buffer (20 mM Tris, pH 7.6, 10 ug/ml acetylated BSA, 50 mM ammonium acetate, 0.1 % (v/v) Tween-20) for 1h at 37° C.

(b) The assay reaction

The equilibrated beads were re-suspended in fresh mutY reaction buffer and ready to be aliquoted into 0.6 ml microcentrifuge tubes. 18 ug of PR beads was aliquoted into each tube, followed by 18 ug of TM beads, 2 ul target (at final concentrations ranging from 0 to $6 \times 10^9$ molecules/tube), and 2.5 ul mutY (5 ng/ul). The final reaction volume in each tube was brought to 30 ul with mutY reaction buffer. Samples containing no TM were also included. These were identical to the above in all aspects except that they contained 18 ug of non-modified streptavidin beads (no DNA immobilized) instead of the TM beads. The tubes were incubated in the dark, at 37° C. for a period of 4.5 to 12 hours.

(c) Detection

Similar to Example 1, detection of the PRF (which is a function of target identification) for initial research was performed via gel-electrophoresis. This was to ensure that methodology could not only identify the cleaved product, but also reveal the cleaved fragment size and provide conclusive evidence of specific cleavage at the designed mismatch site.

Figure 2:
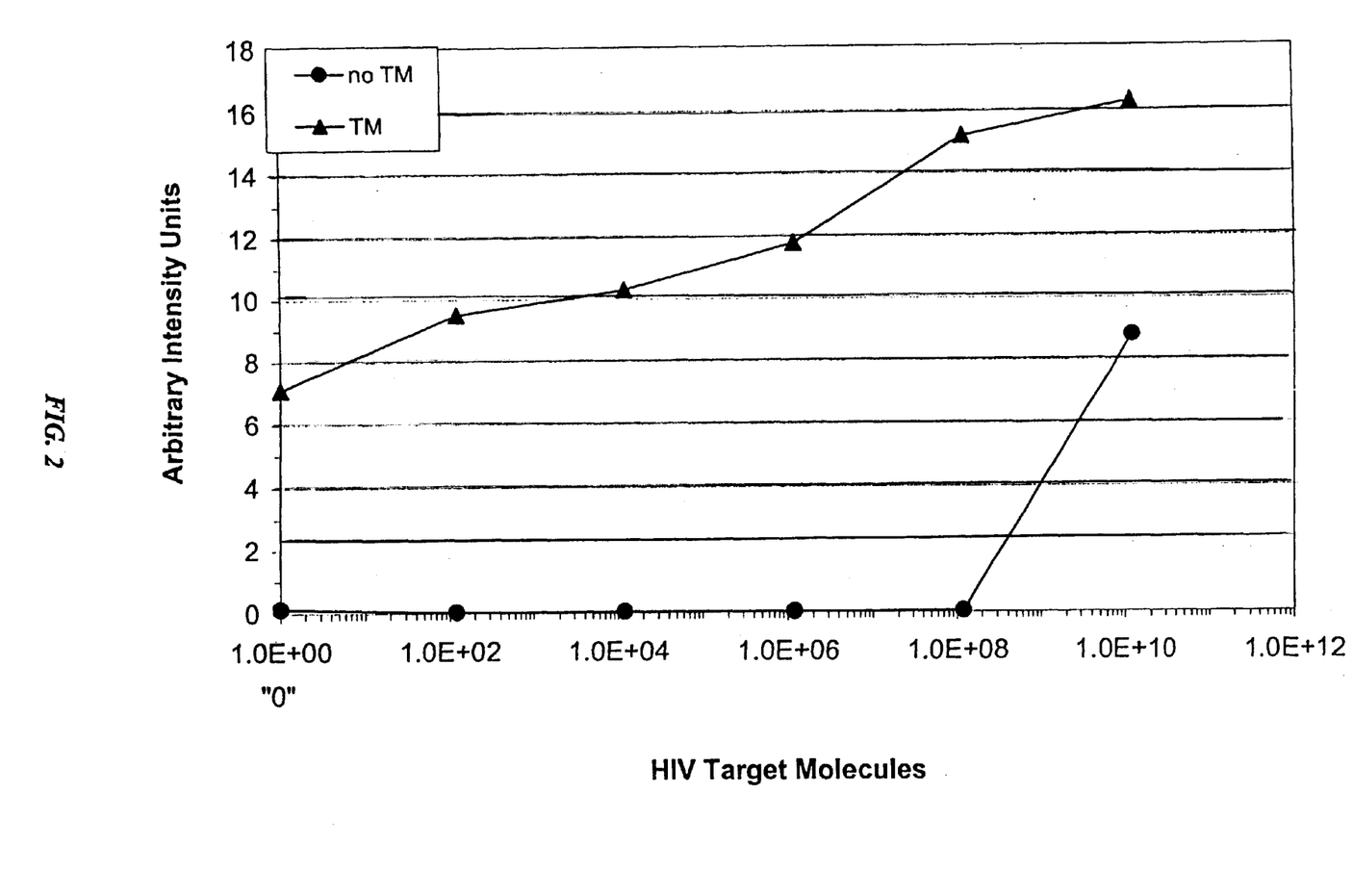
FIG. 2 graphically depicts the results of Example 2.

Following incubation, a 7.5 ul aliquot of the supernatant from each tube was mixed with an equal volume of stop solution (95% (v/v) formamide, 20mM EDTA, 0.05% (w/v) bromophenol blue, 0.05% (w/v) xylene cyanol FF), and subjected to a 20 % PAGE, at 300 V for 45 min (Mini-Protean II Electrophoresis Cell, BioRad, Hercules, Calif.). Gel contents were subsequently transferred to a positively charged nylon membrane (Tropolin-Plus, Tropix, Bedford, Ma.) for 3 h. After drying the membrane completely, the DNA was fixed to the membrane by UV-cross-linking (using a total UV exposure of 120 millijoules/cm² at 254 nm). Chemiluminescent detection of the fluorescein labeled PRF (released into the supernatants of the samples and transferred onto the nylon membrane) was performed using Tropix' Southern Star™ detection kit. Chemiluminescent signal was detected by exposure of the membrane to a film and quantitated. The quantitative results are graphically represented in FIG. 2.

(d) Conclusion

Specific mutY cleavage of the PR:Target duplex is demonstrated. With the inclusion of TM beads in the assay

Example 3

Detection of HIV-1 on Microtiter Wells

This example is similar to Example 2, except that the assay reaction is performed in a microtitre well assay format.
(a) Design of the PR complex and TM entity
  Sequence Selection
  Sequences of PR complex, TM and target are identical to those described in Example 2.
  Immobilization of PR complex and TM
  Reacti-Bind™ Streptavidin Coated Polystyrene Microwell Plates (Pierce, Rockford, Ill.) were washed four times with TBST (50 mM Tris, pH 7.4, 150 mM NaCl, 0.1 % (v/v) Tween 20), immediately prior to use. PR was immobilized to the streptavidin-coated wells by adding 100 ul of a 1 fmol/ul biotinylated PR solution to each well. Similarly, TM and poly A (as the "non-TM" control) were each immobilized to separate, streptavidin-coated wells using biotinylated TM and biotinylated poly A, respectively. After a I h incubation at room temperature, the wells were washed four times with TBST.
b) The assay reaction
  To the PR wells, were added 100 ul of HIV target (final concentrations ranging from 0 to 20 pmol/well) diluted in mutY reaction buffer containing mutY (5 uL). Following a 17 h incubation (in the dark) at 37° C.; 85 ul of supernatant from the PR wells and 15 ul of mutY reaction buffer (containing 2.5 ul muty) were added to TM-immobilized wells. After incubating these wells, in the dark, for 17 h at 370° C., 85 ul of supernatant from the TM wells and 15 ul of mutY solution (containing 12 ng mutY) were pipetted to fresh PR-immobilized wells. This procedure was repeated to a second set of fresh TM wells and then to a third set of PR complex wells.
  In order to demonstrate the amplification effect of TM, negative controls (absence of TM) were also included. For these samples, the supernatant transfer procedure described above, was simultaneously performed between PR wells and the non-TM control (poly A) wells.
c) Detection
  Following the final incubation in the PR wells, a 10 ul aliquot of the supernatant from each well was mixed with an equal volume of stop solution, and subjected to electrophoresis, transfer and detection in a manner identical to that described in Example 2.
d) Conclusion
  MutY cleavage of the target-probe duplex was demonstrated (data not shown). This result demonstrates the potential of performing the assay on a microwell plate format.

Example 4

Detection of Plasmid Containing HIV-1 Sequence

The HIV examples described thus far utilized synthetic oligonucleotides as a target. In this example, a non-synthetic HIV sequence contained within a plasmid was used as the target.

This section is divided into five (5) subsections. These are, (a) target isolation from the plasmid, (b) design of the probe reporter complex (PR complex) and target mimic (TM), (c) the assay reaction, (d) detection of the target of interest, and (e) conclusion. The notable difference between this example and Example 1, aside from the different target sequence, is the utilization of a on-isotopic detection methodology.

The pBENN7 plasmid clone was obtained from the Center for Transfusion Medicine (NIH, Bethesda, Md.). It contains the 5.1 kb EcoRI fragment of pBENN2 extending from -450 in the 5' flanking cellular sequence to 4684 in the LAV proviral sequence. The pBENN7 plasmid was digested with EcoRI restriction enzyme (New England Biolabs, Inc., Beverly, Md.) at 37° C. for 1.5h in 50 ul of NEBuffer EcoRI. Dilutions of digested plasmids were prepared in TE buffer (10 mM Tris-HCl, pH 7.6, 1 mM EDTA), heated at 95° C. for 10 min and placed on ice prior to use in the hybridization reaction.

Immobilization of PR complex and TM
  All immobilization, rinse and wash steps were performed in 0.6-mL microcentrifuige tubes. Streptavidin magnetic beads (Dynal Inc., Lake Success, N.Y.) were rinsed twice in binding buffer. Immobilization of PR (sequence and modifications as described in Example 2) to the streptavidin beads was performed in binding buffer (20 pmol DNA/mg beads, for 30 min at 37° C., with gentle agitation, in the dark). TM (sequence and modification as described in Example 2) was immobilized on separate streptavidin-coated magnetic beads using identical reaction concentrations and conditions.

Following immobilization, the beads were rinsed with binding buffer and washed with washing buffer once for 10 min at 45° C., and four times for 15 min each at 45° C. Prior to utilization in the hybridization and/or amplification reaction, the beads were rinsed and then equilibrated in mutY reaction buffer once for 10 min at 45° C. and twice for 15 min at 45° C.
b) The assay
  Hybridization Reaction
  Equilibrated PR beads were rinsed and resuspended in TBST (50 mM Tris-HCl, pH 7.4, 150 mM NaCl, 0.1 % Tween 20), in 0.6-mL microcentrifuige tubes, at 20 ug/tube. Heat-denatured plasmid (10 ml) at final concentrations ranging from 0 to $44 \times 10^9$ molecules were added to the tubes. After bringing the final reaction volumes to 36 uL, the tubes were incubated for 2.5 h at 45° C., with gentle agitation, in the dark.

Amplification Reaction
  The PR beads from the hybridization reaction were separated using a magnetic separator (Dynal Inc., Success Lake, N.Y.). The hybridization solution was discarded and the beads were washed twice in mutY reaction buffer. For each tube, the beads were then resuspended in 32 ul of amplification reaction mixture containing 2 ul mutY enzyme and 20 ug TM beads in mutY reaction buffer. The tubes were incubated at 37° C. for 18 h, with gentle agitation, in the dark.
c) Detection
  Following incubation, a 10-ul aliquot of the supernatant from each tube was mixed with an equal volume of stop solution, subjected to electrophoresis, transferred and detected in a manner identical to that described in Example 2.
d) Conclusion
  Detection of the HIV target (plasmid insert) down to 44 molecules was accomplished. This result suggests that the assay system of the present invention can be used to detect longer, as well as double stranded target nucleic acids.

Example 5

Alternative Homogenous Assay Formats

The preceding examples relate to non-homogeneous assay formats. However, the present invention is easily adapted to be carried out in a homogeneous assay format. The following examples present three different such formats.

1. Fluorescent-Quenched Label

There are many different well-known methodologies for quenching fluorophore groups. Fluorescein quenching for detection of nucleic acid amplification has also been described. There are two popular arrangements favorable for this amplified assay format:

a. Linear: when a quencher(Q) and fluorophore(F) are placed in close proximity along the probe sequence
b. Hairpin structures ("molecular beacons"): when a quencher(Q) and fluorophore (F) are placed on opposite sides of a hairpin structure, such that they are in close proximity.

a. Linear energy transfer pair

Figure 3:
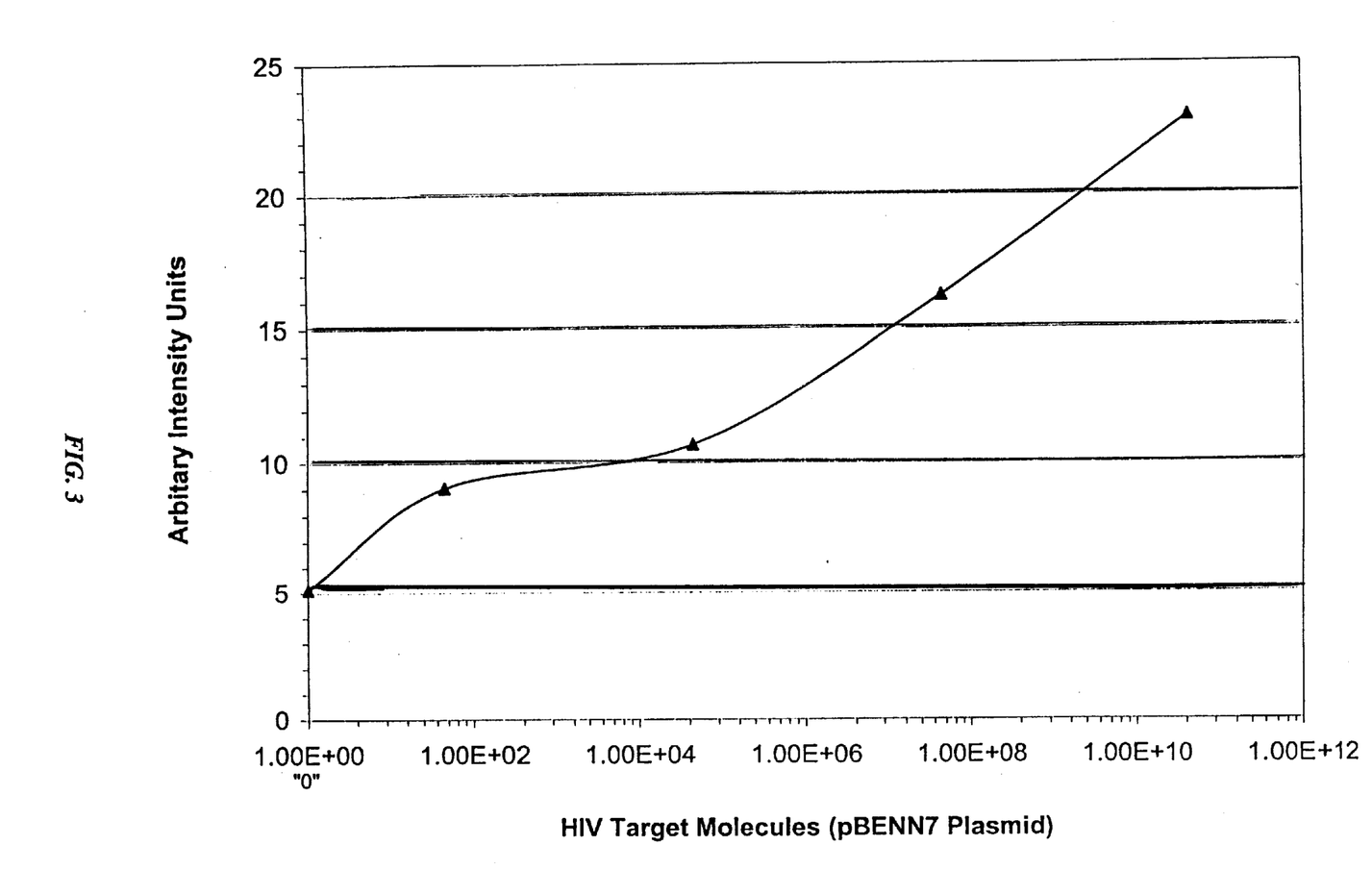
FIG. 3 graphically depicts the results of Example 4.

FIG. 3 depicts a homogeneous assay format when immobilized probe (or target mimic) contains quenched fluorescent label covalently attached to bases in the nucleic acid sequence. As shown, the quencher (Q) and fluorophore (F) are on opposite sides of a mismatch cleavage site (filled circle) which is cleaved in the presence of target. After cleavage, the fluorophore attached to the probe (or target mimic) fragment is free to diffuse away from the quencher and begins emitting a fluorescent signal. Thus, the fluorescence intensity increases in proportion to the amount of target present in the sample.

Design of the PR complex and TM

Internal and terminal labeling is a known method in the art. Many modified synthetic oligonucleotides are commercially available. Biotin can be easily used for immobilization by attaching it to the 5' end of the probe. Fluorescein(F) and DABCYL(Q) can be used as the fluorophore/quencher pair as follows:

Probe: 5' Biotin-aca gct $t^Q$cc tAa ttg at$^F$g gtg tta tag cc 3' (Seq. ID No.7)

Bolded characters represent the following sequence modifications: A is the mismatch site; $t^Q$ is DABCYL modified thymine; $t^F$ is flourescein-modified thymine.

Cleaved probe fragment: 5' a ttg at$^F$g gtg tta tag cc 3' (Seq. ID No. 8)

TM sequence/cleaved probe fragment hybrid:

5'Biotin taa ggc tat aaA acc a tc aat gag gaa gct gt-3' (Seq. ID No. 9)

3'ccg ata ttg tgg $t^F$ag tta 5' (Seq. ID No. 10)

The TM sequence with the cleaved probe fragment shows that mismatch A is at a similar distance from the modified oligonucleotide in the target mimic-cleaved probe hybrid sequence as in the probe-target hybrid sequence.

Immobilization and assay are performed as described in Example 2. Increasing intensity of the fluorescence signal is proportional to the amount of target present in the system. Quantitative measurement of target levels may be obtained by comparison to results obtained for known amount of target used, as calibrators.

b. Hairpin structures

Molecular beacons are a relatively new class of oligonucleotide probes that have a loop (DNA that forms a single stranded loop attached to a double stranded stem) with a fluorophore and a quencher attached to two opposing nucleotides in the stem portion. The fluorophore emits signal only when it is separated from its quencher, for example when the probe hybridizes to the target nucleic acid.

Figure 4:
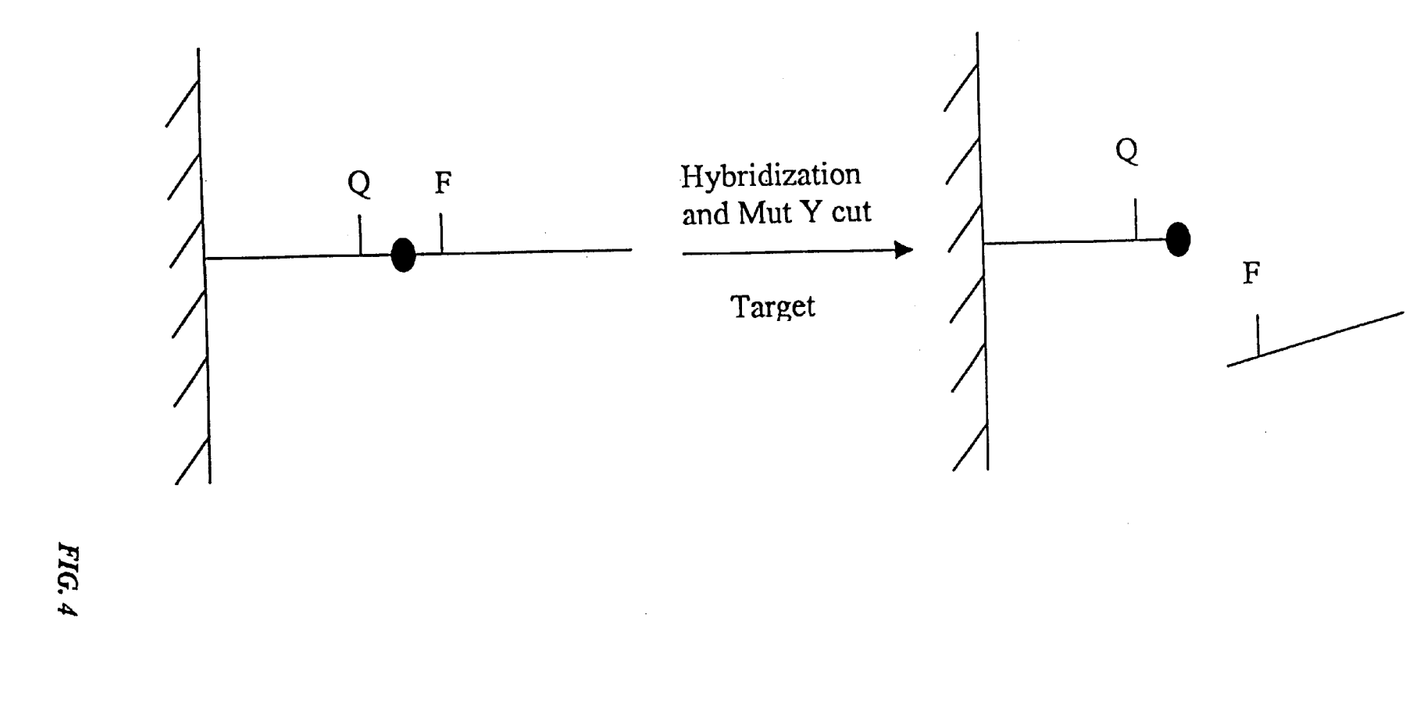
FIG. 4 represents a homogeneous assay using a linear probe as described in Example 5.

As depicted in FIG. 4, the probe is in the form of an immobilized hairpin structure, and contains quenched fluorescent label covalently attached to the stem portion of the probe sequence. The quencher (Q) and fluorophore (F) are in close proximity, and separated by the mismatch cleavage site (filled circle). The hairpin is designed to avoid cleavage of the mismatch when the stem is formed in the probe, i.e. there is no mismatch in the stem itself.

When target hybridizes to the immobilized probe, the hairpin "opens up" (i.e. it becomes linear) and the mismatch site is cleaved by mutY. This causes the quencher and fluorophore to become separated when the probe fluorophore complex is released into the assay medium, which results in a detectable fluorescent signal. As the assay system continues to cycle as described herein, the fluorescence signal is intensified in an amount that is proportional to the amount of target present in the sample solution.

Probe-hairpin and target-mimic design

Biotin is attached to the 5' end of the probe, and then the biotin-probe conjugate is attached to Dynal magnetic streptavidin coated particles. Fluorescein (F) and DABCYL (Q) are attached to the probe as follows:

Probe: 5' Biotin-acagcttcct$^Q$Aatt gatggtgttatagccaatt$^F$3' (Seq. ID NO. 11) 10 15 29 34

Figure 5:
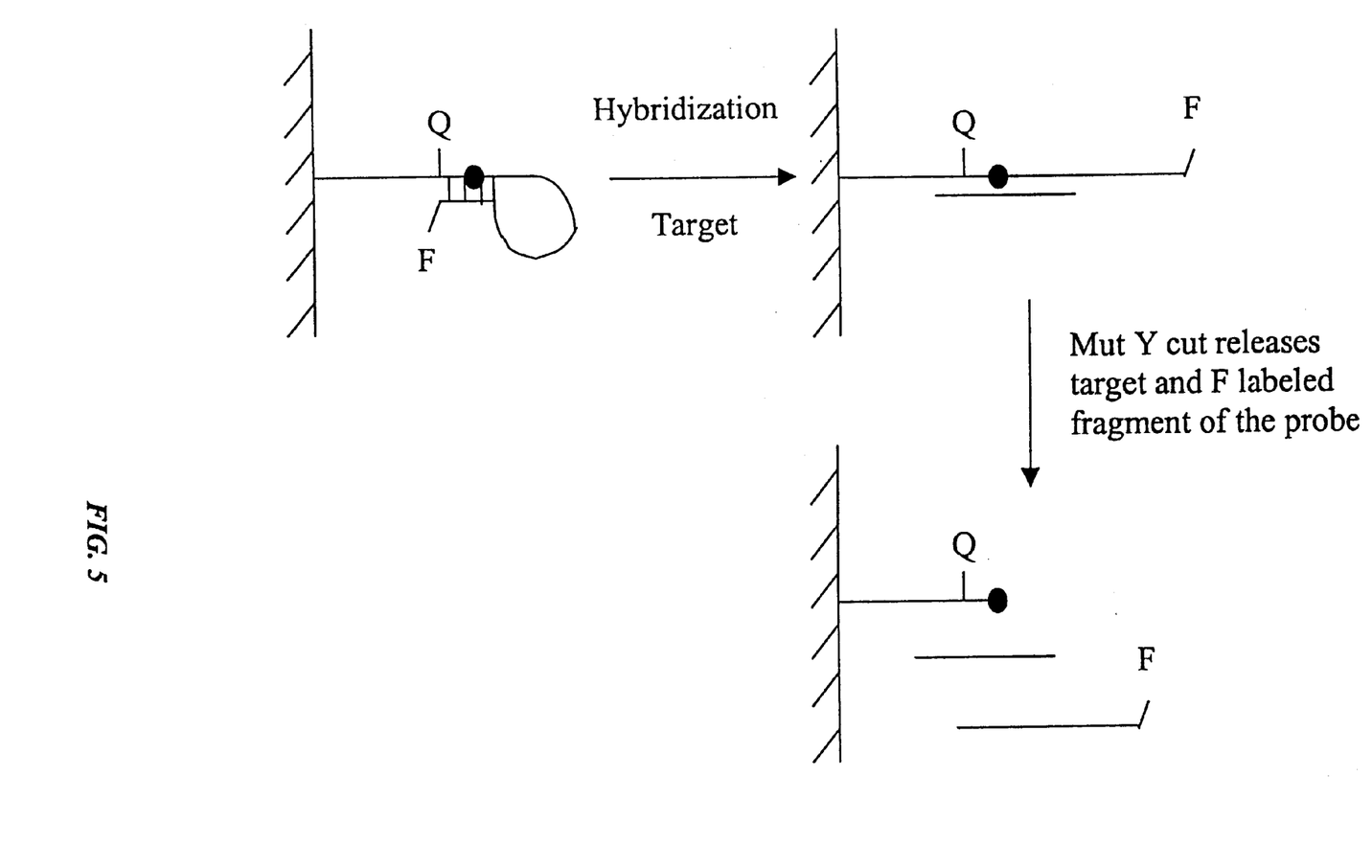
FIG. 5 represents a homogeneous assay using a hairpin probe as described in Example 5.
Figure 6:
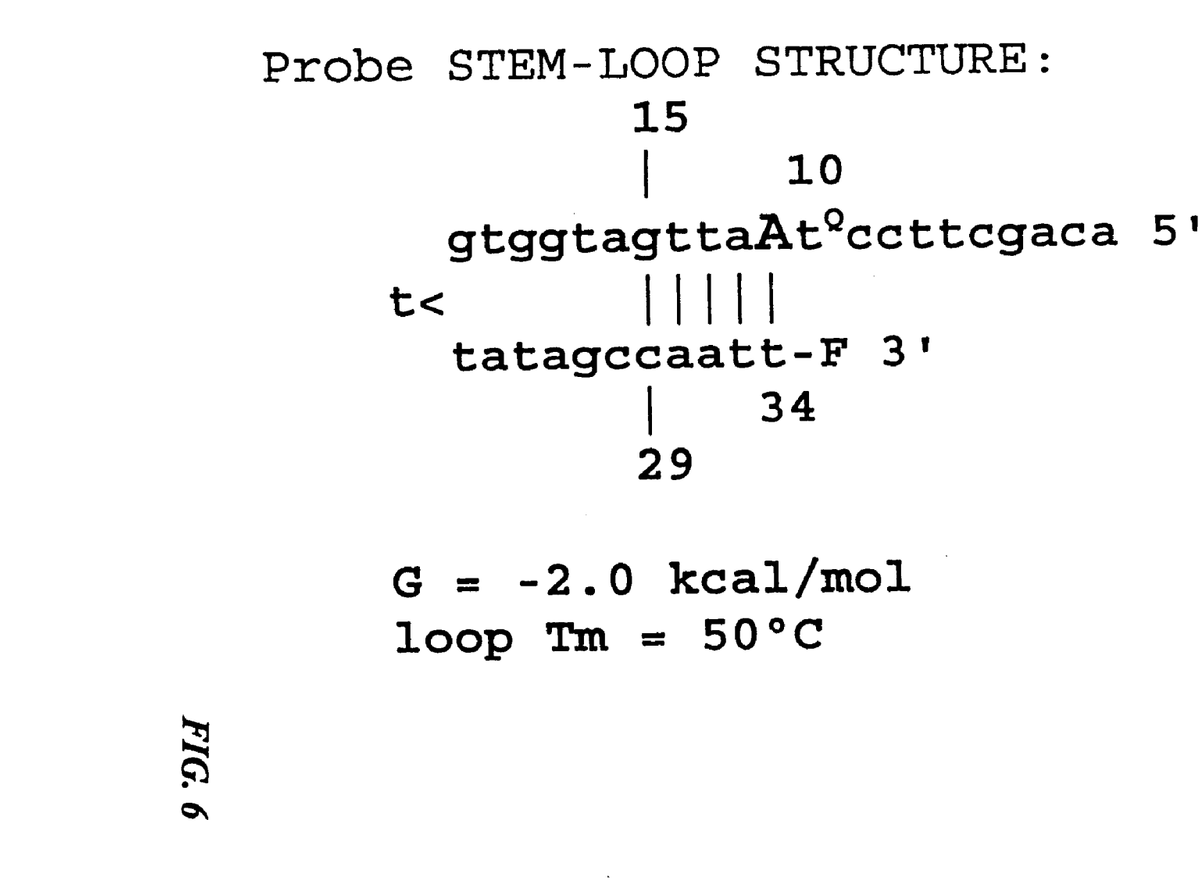
FIG. 6 represents the structure of the hairpin probe depicted in FIG. 4.

As depicted in FIG. 5, the stem forms between nucleotides 10 to 15 and nucleotides 29 to 33. The Tm and energy forces were calculated using a Zuker folding program, and determined to be Tm=50° C. and G=−2.0 kcal/mol, respectively.

This probe can be used to detect the following target sequence:

5'gtg gta gtt aat cct tcg ac 3' (Seq. ID No. 12)

The Tm (by % GC) of the hybrid formed between the probe and the target is around 62° C. (with 1 mismatch).

When target is present in the sample and added to the assay system, it will hybridize to the probe in the stem region, which opens up the hairpin structure. Simultaneously, the mismatch cleavage site is formed and the fluorophore, in the absence of the proximate quencher emits fluorescent signal. The mismatch cleavage reagent cleaves the probe, and the cleaved probe fragment is free to diffuse through the assay medium and bind to an immobilized TM.

Sequence of the cleaved probe fragment:

5'att gat ggt gtt ata gcc aat t-F 3' (Seq. ID No. 13)

TM sequence:

5'Biotin-taa ggc tat aaA acc atc aat gag gaa gct 3' (Seq. ID No. 14)

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A tricyclic assay system for measuring a target nucleic acid from a sample added to an assay medium, comprising:
 a) a non-diffusible first probe-reporter complex (PR), wherein the first probe comprises a nucleotide sequence that is complementary to the target nucleic acid, and wherein the first probe and the target nucleic acid have sufficient complementarity to hybridize to form a first cleavage site;
 b) a first cleavage reagent that recognizes and cleaves the first cleavage site thus forming a diffusable probe fragment-reporter complex and releasing the target nucleic acid into the assay medium;
 c) a non-diffusible first target mimic (TM) that is functionally separated from the probe reporter complex, wherein the first target mimic comprises a nucleotide sequence that is complementary to the probe, and wherein the first target mimic and probe fragment have sufficient complementarity to hybridize to form a second cleavage site; and
 d) a second cleavage reagent, which may be the same or different from the first cleavage reagent, that recognizes and cleaves the second cleavage site thus forming a diffusible target mimic fragment and releasing the probe fragment reporter complex into the assay medium;
 wherein the target mimic fragment has sufficient complementarity to hybridize to a second probe;
 wherein the target nucleic acid after release into the assay medium following cleavage of the first probe remains capable of binding to a second probe; and
 wherein the probe fragment has sufficient complementarity to hybridize to a second target mimic.

2. The assay system according to claim 1, wherein the first and second cleavage sites are mismatch cleavage sites.

3. The assay system according to claim 1, wherein the cleavage reagent is a glycosylase enzyme.

4. The assay system of claim 1, wherein the mismatch cleavage sites are cleavable by an enzyme selected from the group consisting of mutY and mutM.

5. The assay system of claim 1, wherein the probe comprises DNA, RNA or a combination thereof.

6. The assay system of claim 1, wherein the probe is linked directly to the reporter.

7. The assay system of claim 1, wherein the target mimic comprises DNA, RNA or a combination thereof.

8. The assay system of claim 2, wherein the first cleavage site consists of a single nucleic acid base pair mismatch between the probe and the target.

9. The assay system of claim 2, wherein the second cleavage site consists of a single nucleic acid base pair mismatch between the probe fragment and the target mimic.

10. The assay system of claim 1, wherein the PR complex and the TM are immobilized on at least one solid surface or support.

11. The assay system of claim 1, wherein a third cleavage site is formed through the complementarity of the target mimic fragment to the second probe.

12. The assay system of claim 11, wherein the third cleavage site is a mismatch cleavage site.

13. The assay system of claim 12, wherein the third cleavage site consists of a single nucleic acid base pair mismatch between the probe and the target mimic fragment.

14. The assay system of claim 10, wherein the solid surfaces are selected from the group consisting of silicon, plastic, nylon, glass, ceramic, photoresist or rubber surface.

15. The assay system of claim 10, wherein the PR complex and the TM are immobilized on separate locations on the same solid surface.

\* \* \* \* \*

SEQUENCE LISTING

<160> NUMBER OF SEQ ID NOS: 15

<210> SEQ ID NO 1
<211> LENGTH: 32
<212> TYPE: DNA
<213> ORGANISM: Artificial Sequence
<220> FEATURE:
<223> OTHER INFORMATION: Modified sequence of probe reporter complex

<400> SEQUENCE: 1
gactggcggc tcaaagggca cgacactatg tc                                32

<210> SEQ ID NO 2
<211> LENGTH: 33
<212> TYPE: DNA
<213> ORGANISM: Artificial Sequence
<220> FEATURE:
<223> OTHER INFORMATION: Oligonucleotide used as actual sequence

<400> SEQUENCE: 2
gactttcgac atagtgtagt gccctgtgag ccg                               33

<210> SEQ ID NO 3
<211> LENGTH: 15
<212> TYPE: DNA
<213> ORGANISM: Artificial Sequence
<220> FEATURE:
<223> OTHER INFORMATION: Target sequence

<400> SEQUENCE: 3
gccgagtgtc ccgtg                                                   15

<210> SEQ ID NO 4
<211> LENGTH: 29
<212> TYPE: DNA
<213> ORGANISM: Artificial Sequence
<220> FEATURE:
<223> OTHER INFORMATION: Probe reporter sequence

<400> SEQUENCE: 4
acagcttcct aattgatggt gttatagcc                                    29

<210> SEQ ID NO 5
<211> LENGTH: 32
<212> TYPE: DNA
<213> ORGANISM: Artificial Sequence
<220> FEATURE:
<223> OTHER INFORMATION: Oligonucleotide used as actual sequence

<400> SEQUENCE: 5
taaggctata aaaccatcaa tgaggaagct gt                                32

<210> SEQ ID NO 6
<211> LENGTH: 20
<212> TYPE: DNA
<213> ORGANISM: Artificial Sequence
<220> FEATURE:
<223> OTHER INFORMATION: Target sequence

<400> SEQUENCE: 6
taccatcaat gaggaagctg                                              20

<210> SEQ ID NO 7
<211> LENGTH: 29

```
<212> TYPE: DNA
<213> ORGANISM: Artificial Sequence
<220> FEATURE:
<223> OTHER INFORMATION: Probe

<400> SEQUENCE: 7
acagcttcct aattgatggt gttatagcc                                29

<210> SEQ ID NO 8
<211> LENGTH: 18
<212> TYPE: DNA
<213> ORGANISM: Artificial Sequence
<220> FEATURE:
<223> OTHER INFORMATION: Cleaved probe fragment

<400> SEQUENCE: 8
attgatggtg ttatagcc                                            18

<210> SEQ ID NO 9
<211> LENGTH: 32
<212> TYPE: DNA
<213> ORGANISM: Artificial Sequence
<220> FEATURE:
<223> OTHER INFORMATION: Cleaved probe fragment hybrid

<400> SEQUENCE: 9
taaggctata aaccatcaa tgaggaagct gt                             32

<210> SEQ ID NO 10
<211> LENGTH: 18
<212> TYPE: DNA
<213> ORGANISM: Artificial Sequence
<220> FEATURE:
<223> OTHER INFORMATION: Cleaved probe fragment hybrid/TM sequence

<400> SEQUENCE: 10
attgatggtg ttatagcc                                            18

<210> SEQ ID NO 11
<211> LENGTH: 33
<212> TYPE: DNA
<213> ORGANISM: Artificial Sequence
<220> FEATURE:
<223> OTHER INFORMATION: Probe

<400> SEQUENCE: 11
acagcttcct aattgatggt gttatagcca att                           33

<210> SEQ ID NO 12
<211> LENGTH: 20
<212> TYPE: DNA
<213> ORGANISM: Artificial Sequence
<220> FEATURE:
<223> OTHER INFORMATION: Probe

<400> SEQUENCE: 12
gtggtagtta atccttcgac                                          20

<210> SEQ ID NO 13
<211> LENGTH: 22
<212> TYPE: DNA
<213> ORGANISM: Artificial Sequence
<220> FEATURE:
<223> OTHER INFORMATION: Cleaved probe fragment sequence

<400> SEQUENCE: 13
```

```
attgatggtg ttatagccaa tt                                    22

<210> SEQ ID NO 14
<211> LENGTH: 30
<212> TYPE: DNA
<213> ORGANISM: Artificial Sequence
<220> FEATURE:
<223> OTHER INFORMATION: TM sequence

<400> SEQUENCE: 14
taaggctata aaaccatcaa tgaggaagct                            30

<210> SEQ ID NO 15
<211> LENGTH: 11
<212> TYPE: DNA
<213> ORGANISM: Artificial Sequence
<220> FEATURE:
<223> OTHER INFORMATION: Probe STEM-LOOP structure

<400> SEQUENCE: 15
tatagccaat t                                                11
```